United States Patent
Tarui et al.

(10) Patent No.: US 8,264,243 B2
(45) Date of Patent: Sep. 11, 2012

(54) LIQUID CONCENTRATION SENSING DEVICE

(75) Inventors: Jun Tarui, Kariya (JP); Akikazu Uchida, Obu (JP); Toshiki Annoura, Nagoya (JP); Hiroshi Katsurahara, Anjo (JP); Takayoshi Nakamura, Kiyosu (JP)

(73) Assignee: Denso Corporation, Kariya (JP)

( * ) Notice: Subject to any disclaimer, the term of this patent is extended or adjusted under 35 U.S.C. 154(b) by 375 days.

(21) Appl. No.: 12/761,512

(22) Filed: Apr. 16, 2010

(65) Prior Publication Data

US 2010/0264937 A1 Oct. 21, 2010

(30) Foreign Application Priority Data

Apr. 16, 2009 (JP) .................................. 2009-99629

(51) Int. Cl.
*G01R 27/22* (2006.01)
(52) U.S. Cl. .................... 324/663; 324/674; 324/658
(58) Field of Classification Search .................. None
See application file for complete search history.

(56) References Cited

U.S. PATENT DOCUMENTS

| 5,033,293 A | * | 7/1991 | Honma et al. ............. 73/114.38 |
| 5,367,264 A | | 11/1994 | Brabetz |

FOREIGN PATENT DOCUMENTS

JP 2010249669 A * 11/2010

* cited by examiner

*Primary Examiner* — Paresh Patel
(74) *Attorney, Agent, or Firm* — Nixon & Vanderhye PC

(57) ABSTRACT

A capacitance sensing section senses a capacitance between first and second electrodes. A temperature sensing section senses fuel temperature. A microcomputer functions as a concentration sensing section and senses a concentration of ethanol contained in fuel based on the capacitance sensed by the capacitance sensing section and the temperature sensed by the temperature sensing section. The microcomputer functions as an abnormality detecting section and performs abnormality determination to determine that an abnormality has occurred in the capacitance sensing section when the capacitance sensed by the capacitance sensing section does not change and the temperature sensed by the temperature sensing section changes. Since a dielectric constant has such a temperature characteristic that the dielectric constant changes with the temperature, the abnormality detecting section can detect occurrence of the abnormality in the capacitance sensing section.

8 Claims, 7 Drawing Sheets

FIG. 7

|  | $\Delta T$ | $\Delta Cp$ |
|---|---|---|
| E100 | 20°C | 5 |
| E80 | 20°C | 4 |
| E60 | 20°C | 3 |
| E40 OR LOWER | NOT DETECTED ||

# LIQUID CONCENTRATION SENSING DEVICE

CROSS REFERENCE TO RELATED APPLICATION

This application is based on and incorporates herein by reference Japanese Patent Application No. 2009-99629 filed on Apr. 16, 2009.

BACKGROUND OF THE INVENTION

1. Field of the Invention

The present invention relates to a liquid concentration sensing device that senses a concentration of a sensed liquid based on a capacitance.

2. Description of Related Art

In the case of an engine that uses ethanol-blended gasoline as fuel, generally, an ethanol concentration in the fuel is sensed with a liquid concentration sensing device provided in a fuel supply system, and fuel injection quantity, ignition timing and the like are controlled according to the ethanol concentration. Thus, deterioration of exhaust gas is inhibited and drivability is improved. The liquid concentration sensing device senses the ethanol concentration in the fuel by sensing a capacitance and fuel temperature between two electrodes immersed in the fuel. There has been a possibility that a conventional liquid concentration sensing device erroneously senses the ethanol concentration in the fuel when an abnormality occurs in a capacitance sensing device that senses the capacitance.

A measuring instrument described in Patent document 1 (PCT patent application Japanese translation No. H05-507561) senses an alcohol concentration by sensing a capacitance between two electrodes, which use a mixture gas consisting of alcohol and gasoline as a dielectric, in the form of an output frequency of an operational amplifier electrically connected to the electrodes. If the alcohol concentration lowers and the capacitance decreases, there is a possibility that the output frequency of the operational amplifier turns into an undetectable frequency. In order to prevent such the possibility, the measuring instrument has an additional capacitor connected with the two electrodes in parallel.

However, in the case where the measuring instrument is constructed as described in Patent document 1, the operational amplifier oscillates at a frequency corresponding to the additional capacitor if an abnormality such as a disconnection arises between the two electrodes and the operational amplifier. Accordingly, abnormality detection becomes difficult.

SUMMARY OF THE INVENTION

It is an object of the present invention to provide a liquid concentration sensing device enabling abnormality detection.

According to a first example aspect of the present invention, a liquid concentration sensing device has a capacitance sensing section, a temperature sensing section, a concentration sensing section and an abnormality detecting section. The capacitance sensing section senses a capacitance of a sensed liquid. The temperature sensing section senses temperature of the sensed liquid. The concentration sensing section senses a concentration of the sensed liquid based on the capacitance sensed by the capacitance sensing section and the temperature sensed by the temperature sensing section. The abnormality detecting section performs abnormality determination for determining that an abnormality has occurred in the capacitance sensing section when the temperature sensed by the temperature sensing section changes and the capacitance sensed by the capacitance sensing section does not change.

A dielectric constant has such a temperature characteristic that the dielectric constant changes with temperature. Therefore, the abnormality detecting section can detect occurrence of an abnormality in the capacitance sensing section.

However, it is anticipated that the capacitance does not change even if the temperature changes when the temperature increases in synchronization with the increase of the concentration of the sensed liquid or when the temperature decreases in synchronization with the decrease of the concentration of the sensed liquid.

Therefore, according to a second example aspect of the present invention, the abnormality detecting section performs abnormality confirming processing for confirming the occurrence of the abnormality in the capacitance sensing section when the abnormality determination continues for a predetermined period or the abnormality determination occurs multiple times continuously.

Thus, when the state where the capacitance does not change but the temperature changes is temporary, the abnormality detecting section can prevent erroneous detection of the abnormality in the capacitance sensing section. A pace of the abnormality detection can be adjusted by arbitrarily setting the predetermined period.

According to a third example aspect of the present invention, the abnormality detecting section cancels the abnormality determination, which was performed in the past, if the abnormality detecting section detects occurrence of a change in the capacitance sensed by the capacitance sensing section.

If the capacitance sensed by the capacitance sensing section changes, it is thought that the abnormality determination performed in the past is temporary determination caused because the temperature and the capacitance changed in synchronization with each other. Therefore, the abnormality detecting section cancels the abnormality determination performed in the past, whereby the abnormality detecting section can perform correct abnormality detection.

According to a fourth example aspect of the present invention, the abnormality detecting section determines existence or nonexistence of a change in certain one of sensing results of the capacitance sensing section and the temperature sensing section, the certain one having quicker response to a change in the sensed liquid. After that, the abnormality detecting section determines existence or nonexistence of a change in the other one of the sensing results, the other one having slower response to the change in the sensed liquid.

Supposing that the existence/nonexistence of the change in the latter sensing result having the slower response is determined and then the existence/nonexistence of the change in the former sensing result having the quicker response is determined, it is anticipated that the change in the former sensing result having the quicker response has ended when the change in the latter sensing result having the slower response is determined. Therefore, by determining the existence/nonexistence of the change in the former sensing result having the quicker response and then determining the existence/nonexistence of the change in the latter sensing result having the slower response, correct abnormality detection can be performed.

According to a fifth example aspect of the present invention, the abnormality detecting section determines that the capacitance sensed by the capacitance sensing section has not changed if the change amount of the capacitance sensed by the capacitance sensing section is equal to or smaller than a first threshold value set at a value smaller than a change amount of the capacitance, which occurs with respect to a predetermined temperature range in the case of the sensed liquid having a specific concentration.

Thus, the detection accuracy of the abnormality detecting section can be improved by setting the first threshold value at the value close to the change amount of the capacitance, which occurs with respect to the predetermined temperature range according to the temperature characteristic in the case of the sensed liquid having the specific concentration.

According to a sixth example aspect of the present invention, the abnormality detecting section determines that the temperature sensed by the temperature sensing section has changed when a change amount of the temperature sensed by the temperature sensing section is larger than a second threshold value, which is set as a temperature range enabling the abnormality detecting section to detect the change amount of the capacitance that changes according to a temperature change in the case of the sensed liquid having a specific concentration.

There is a case where the change amount of the capacitance due to the temperature change in a fixed range is smaller than detectability of the abnormality detecting section depending on the sensed liquid. Even in such the case, the abnormality detecting section can perform the correct abnormality determination by setting the second threshold value.

According to a seventh example aspect of the present invention, the liquid concentration sensing device further has a determination processing prohibiting section for prohibiting the abnormality detecting section from performing the abnormality determination when the concentration of the sensed liquid sensed by the concentration sensing section is equal to or lower than a predetermined concentration, below which the abnormality detecting section cannot detect the change in the capacitance due to the temperature characteristic.

Erroneous detection can be prevented by prohibiting the abnormality determination of the abnormality detecting section when it is difficult for the abnormality detecting section to detect the change of the capacitance because the concentration of the sensed liquid is low and the change in the capacitance due to the temperature characteristic is small.

According to an eighth example aspect of the present invention, the liquid concentration sensing device further has a determination processing suspending section for suspending the abnormality determination of the abnormality detecting section for a predetermined period when the determination processing suspending section detects that the sensed liquid is replaced.

When the sensed liquid is replaced, there arises a high possibility that the capacitance and the temperature of the sensed liquid change in synchronization with each other. Erroneous detection can be prevented by prohibiting the abnormality determination of the abnormality detecting section in such the case. The predetermined period for suspending the abnormality determination of the abnormality detecting section is a period, in which the replacement of the sensed liquid affects the abnormality detection after the sensed liquid is replaced.

BRIEF DESCRIPTION OF THE DRAWINGS

Features and advantages of embodiments will be appreciated, as well as methods of operation and the function of the related parts, from a study of the following detailed description, the appended claims, and the drawings, all of which form a part of this application. In the drawings:

FIG. 7 is a diagram showing a first threshold value and a second threshold value of the liquid concentration sensing device according to the first embodiment;

DETAILED DESCRIPTION OF EXAMPLE EMBODIMENTS

Hereafter, embodiments of the present invention will be described with reference to the drawings.

First Embodiment

Figure 1:
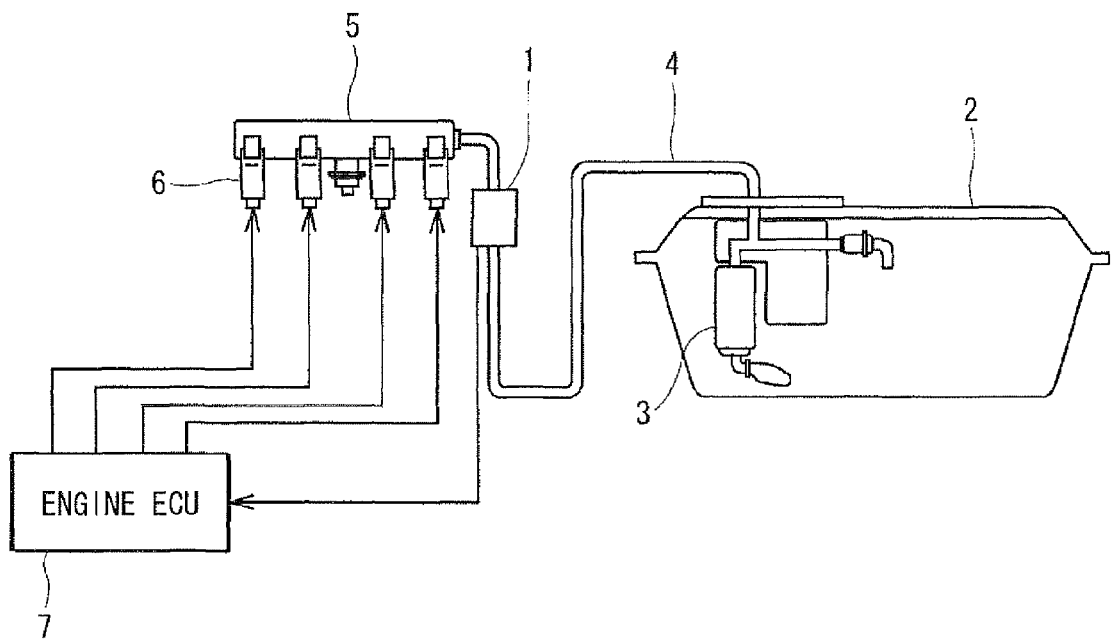
FIG. 1 is a configuration diagram showing a fuel supply system using a liquid concentration sensing device according to a first embodiment of the present invention.

A liquid concentration sensing device according to a first embodiment of the present invention is an ethanol concentration sensing device that senses a concentration of ethanol, which is contained in fuel as a sensed liquid. As shown in FIG. 1, the liquid concentration sensing device is provided in a fuel supply system of an engine for an automobile. An ethanol concentration sensor 1 is provided to a fuel pipe 4 that connects a fuel tank 2 and a delivery pipe 5. The fuel in the fuel tank 2 is pumped by a fuel pump 3 to the delivery pipe 5 through the fuel pipe 4 and is injected from an injector 6 into an intake pipe or a cylinder (not shown). The ethanol concentration sensed by the ethanol concentration sensor 1 is transmitted to an ECU 7 (electronic control unit) of the engine. The ECU 7 controls fuel injection quantity, ignition timing and the like of the fuel injected from the injector 6 in accordance with the ethanol concentration, thereby providing appropriate engine torque characteristics. Thus, the ECU 7 provides good drivability and reduces harmful substances contained in the exhaust gas.

Figure 2:
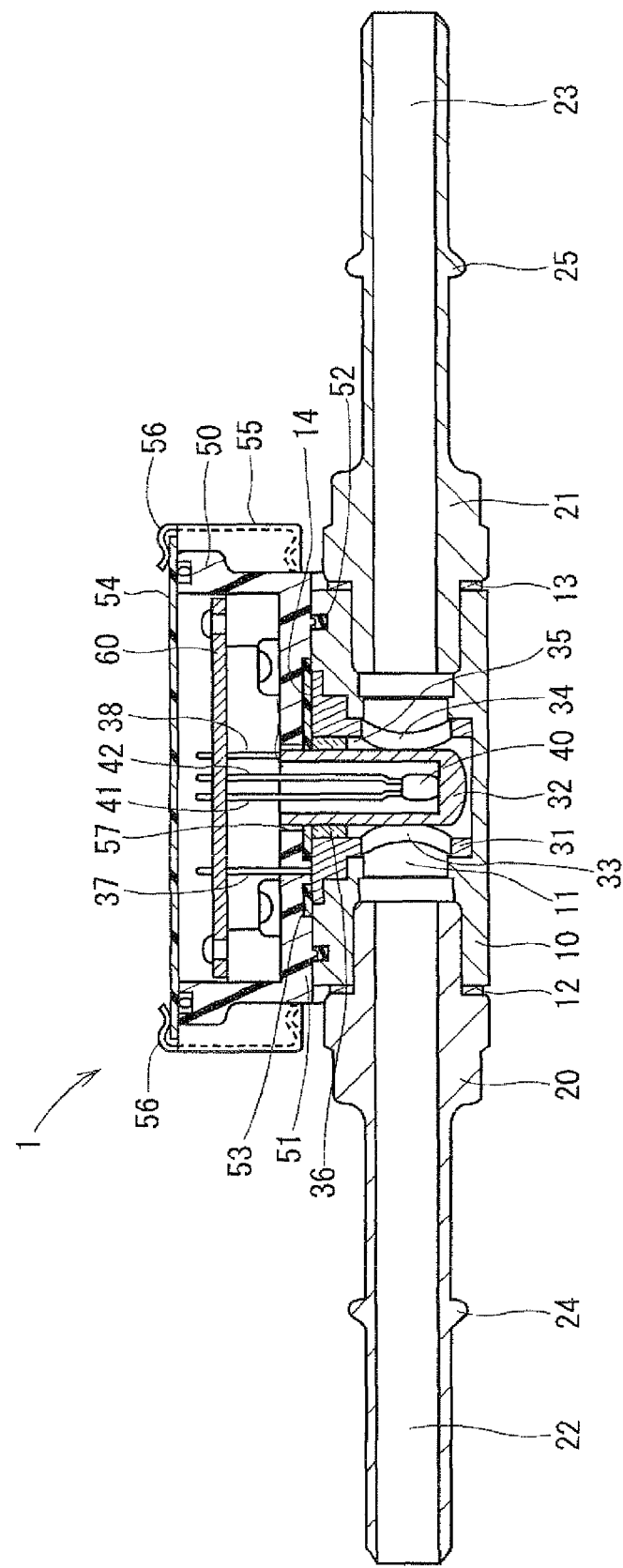
FIG. 2 is a cross-sectional view showing the liquid concentration sensing device according to the first embodiment.

As shown in FIG. 2, the ethanol concentration sensor 1 consists of a first housing 10, connection pipes 20, 21, first and second electrodes 31, 32, a thermistor 40, a second housing 50, a circuit 60 and the like. The first housing 10 is formed substantially in the shape of a cylinder from metal such as stainless steel. The first housing 10 has a fuel chamber 11 inside. The connection pipes 20, 21 are connected to both axial ends of the first housing 10 by thread connection via sealing members 12, 13. The connection pipes 20, 21 are formed in the shapes of cylinders respectively from metal such as stainless steel and have passages 22, 23 inside respectively. Claws 24, 25 are formed on the connection pipes 20, 21 respectively such that the claws 24, 25 protrude radially from middle portions of long sides of the connection pipes 20, 21 respectively. The connection pipes 20, 21 are connected with the fuel pipe 4 via connectors (not shown) connected to the claws 24, 25. Thus, the fuel is supplied to the passages 22, 23 of the connection pipes 20, 21 and the fuel chamber 11 of the first housing 10.

The first electrode 31 is formed substantially in a cylindrical shape from metal such as stainless steel. The first electrode 31 is inserted into the fuel chamber 11 of the first housing 10 from an opening 14 formed in the first housing 10 in a radial direction. The second electrode 32 is formed in the shape of a cylinder having a bottom from metal such as stainless steel. The second electrode 32 is accommodated in a space 35 radially inside the first electrode 31. A radially inner wall of the first electrode 31 and a radially outer wall of the second electrode 32 are fixed with each other by a sealing glass 36. The sealing glass 36 electrically insulates the first electrode 31 and the second electrode 32. The first electrode 31 has fuel holes 33, 34 extending in a radial direction of the first electrode 31. Therefore, the fuel flows from the fuel chamber 11 of the first housing 10 into the space 35 provided between the first electrode 31 and the second electrode 32 via the fuel holes 33, 34. Thus, the first electrode 31 and the second electrode 32 function as a capacitor that uses the fuel as a dielectric.

The thermistor 40 as a temperature sensing device is a temperature sensing element that changes its electrical resistance due to temperature change. The thermistor 40 is accommodated radially inside the second electrode 32 and is in contact with an inner wall of a bottom portion of the second electrode 32. Therefore, the temperature of the fuel in the space 35 between the first electrode 31 and the second electrode 32 is conducted to the thermistor 40 via board thickness of the second electrode 32. A heat conduction member such as a heat radiation grease may be filled between the inner wall of the bottom portion of the second electrode 32 and the thermistor 40.

The second housing 50 is formed in the shape of a cylinder having a bottom from resin or the like, for example. A bottom portion 51 of the second housing 50 is fixed to a radially outer wall of the first housing 10 to block the opening 14 of the first housing 10. An annular packing 52 and a plate-shaped elastic member 53 are held between the second housing 50 and the first housing 10. The packing 52 prevents water and the like from entering a space between the second housing 50 and the first housing 10 from an exterior. The elastic member 53 presses the first electrode 31 against the first housing 10.

A plate-shaped lid 54 is provided to an opening of the second housing 50 to prevent the water and the like from entering an inside of the second housing 50 from the exterior. The lid 54 is fixed by a plate-shaped spring 56 engaged to an engagement section 55 protruding radially outward from the second housing 50. An accommodation hole 57 is formed in the bottom portion 51 of the second housing 50 to accommodate an end portion of the second electrode 32.

The circuit 60 consists of multiple electronic components provided on a printed wiring board and is accommodated inside the second housing 50. A first conductor 37 connects the circuit 60 and the first electrode 31. A second conductor 38 connects the circuit 60 and the second electrode 32. Third and fourth conductors 41, 42 connect the circuit 60 and the thermistor 40.

Figure 3:
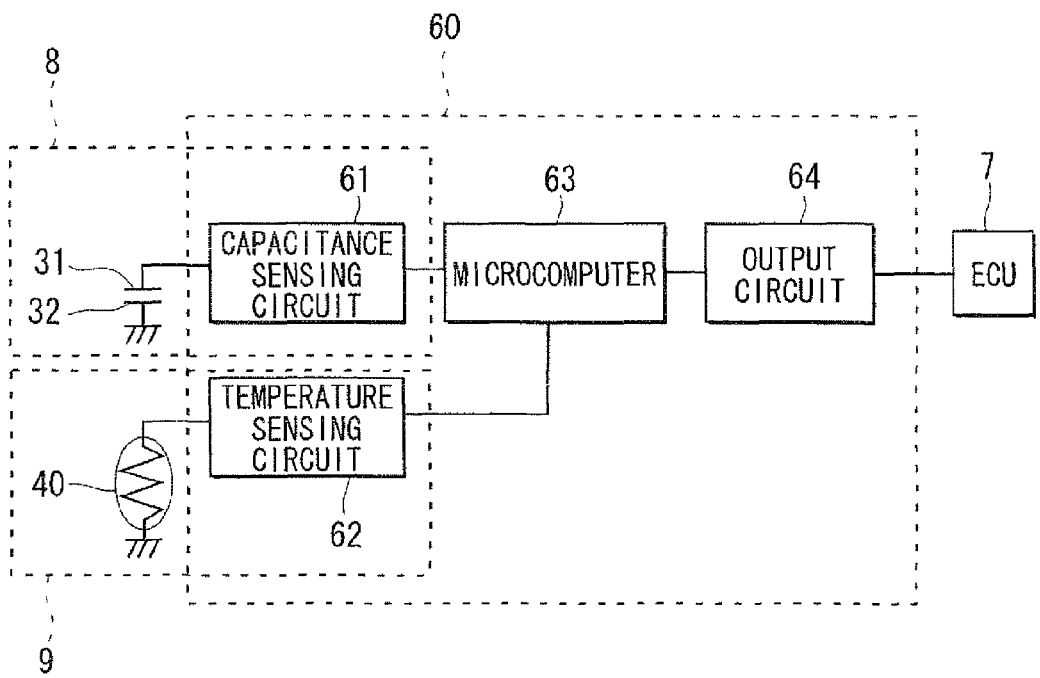
FIG. 3 is a configuration diagram showing a circuit of the liquid concentration sensing device according to the first embodiment.

The circuit 60 consists of a capacitance sensing circuit 61, a temperature sensing circuit 62, a microcomputer 63, an output circuit 64 and the like as shown in FIG. 3. The capacitance sensing circuit 61 senses a capacitance by charge and discharge between the first electrode 31 and the second electrode 32. The temperature sensing circuit 62 senses the fuel temperature between the first electrode 31 and the second electrode 32 by energization to the thermistor 40.

The first and second electrodes 31, 32, the capacitance sensing circuit 61 and the first and second conductors 37, 38 constitute a capacitance sensing section 8. The thermistor 40, the temperature sensing circuit 62 and the third and fourth conductors 41, 42 constitute a temperature sensing section 9.

Figure 4:
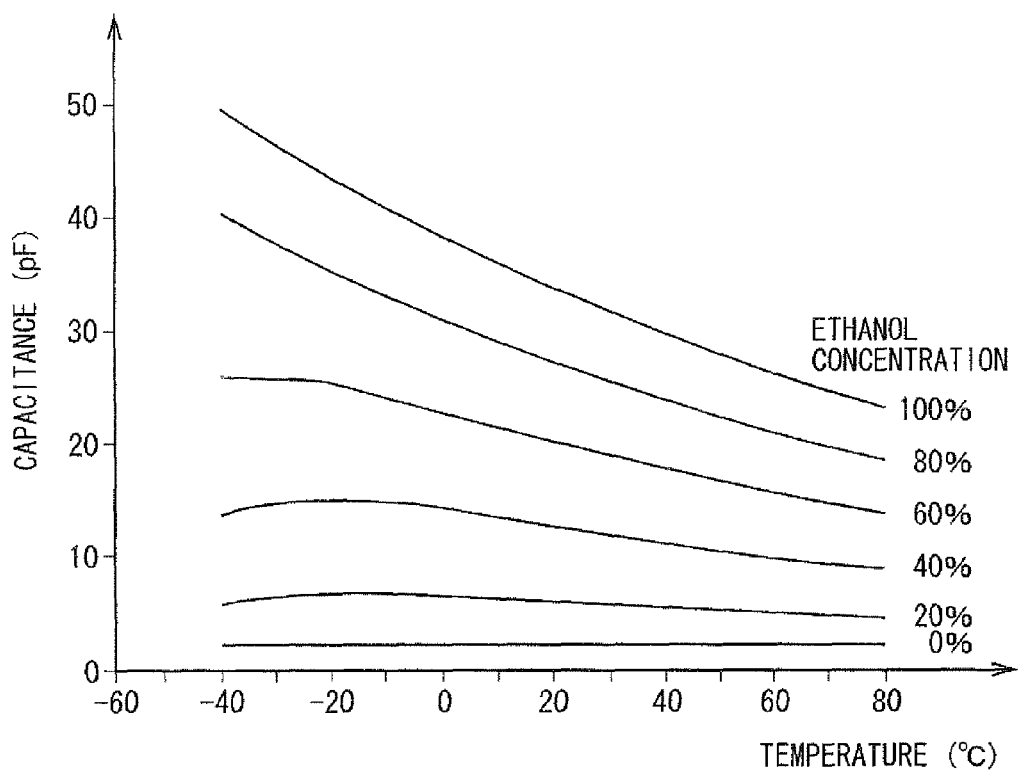
FIG. 4 is a characteristic diagram showing relationships among an ethanol concentration, temperature and a capacitance.

The microcomputer 63 is constituted by CPU, ROM, RAM and the like. The CPU executes programs stored in the ROM, the RAM and the like, whereby the microcomputer 63 functions as a concentration sensing section, an abnormality detecting section and the like. A dielectric constant of the fuel has such a temperature characteristic that the dielectric constant changes with the temperature. As shown in FIG. 4, the capacitance and the temperature have a correlation in the case of fuel having a specific ethanol concentration. That is, in the case of the fuel having the specific ethanol concentration, the capacitance decreases as the temperature increases in a range of temperature equal to or higher than −20 degrees C. Therefore, the concentration sensing section can sense the concentration of the ethanol contained in the fuel based on the capacitance sensed by the capacitance sensing section 8 and the fuel temperature sensed by the temperature sensing section 9.

The abnormality detecting section performs abnormality detection for detecting that an abnormality has occurred in the capacitance sensing section 8 when the temperature sensed by the temperature sensing section 9 changes but the capacitance sensed by the capacitance sensing section 8 does not change. The output circuit 64 transmits the ethanol concentration sensed by the concentration sensing section and the abnormality in the capacitance sensing section 8 detected by the abnormality detecting section to the ECU 7.

Figure 5:
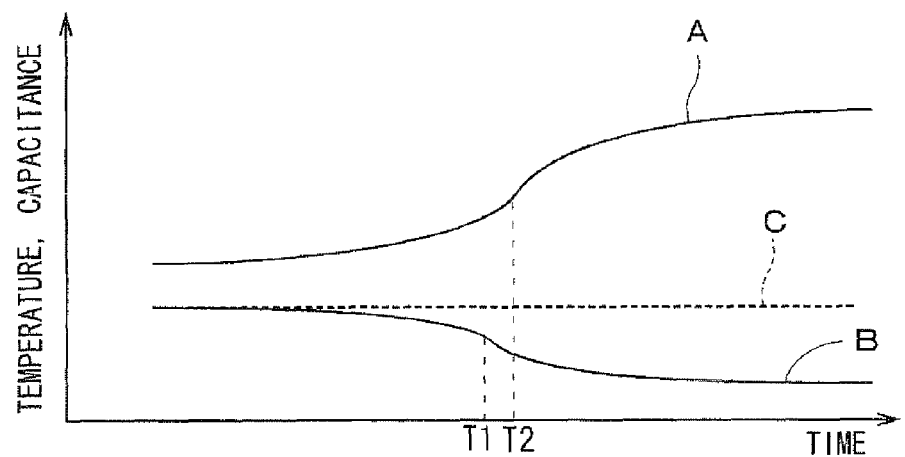
FIG. 5 is a characteristic diagram showing a relationship between a temperature change and a capacitance change of fuel in the fuel supply system using the liquid concentration sensing device according to the first embodiment.

Next, a method of the abnormality detection performed by the abnormality detecting section according to the present embodiment will be explained based on FIG. 5. After the engine starts, the temperature sensed by the temperature sensing section 9 increases with an elapse of time as shown by a solid line A. The capacitance sensed by the capacitance sensing section 8 decreases with the increase of the temperature as shown by a solid line B. The change of the temperature sensed by the temperature sensing section 9 is detected in retard of the change of the capacitance sensed by the capacitance sensing section 8 by a time period from T1 to T2 shown in FIG. 5 because of the heat conduction through the board thickness of the second electrode 32. If an abnormality occurs in any one of the first and second electrodes 31, 32, the capacitance sensing circuit 61 and the first and second conductors 37, 38, it is anticipated that the sensing value of the capacitance sensing section 8 takes a constant value as shown by a broken line C in FIG. 5. In this case, if the temperature sensed by the temperature sensing section 9 changes, the abnormality detecting section can detect that the output value of the capacitance sensing section 8 is an abnormal value.

Figure 6:
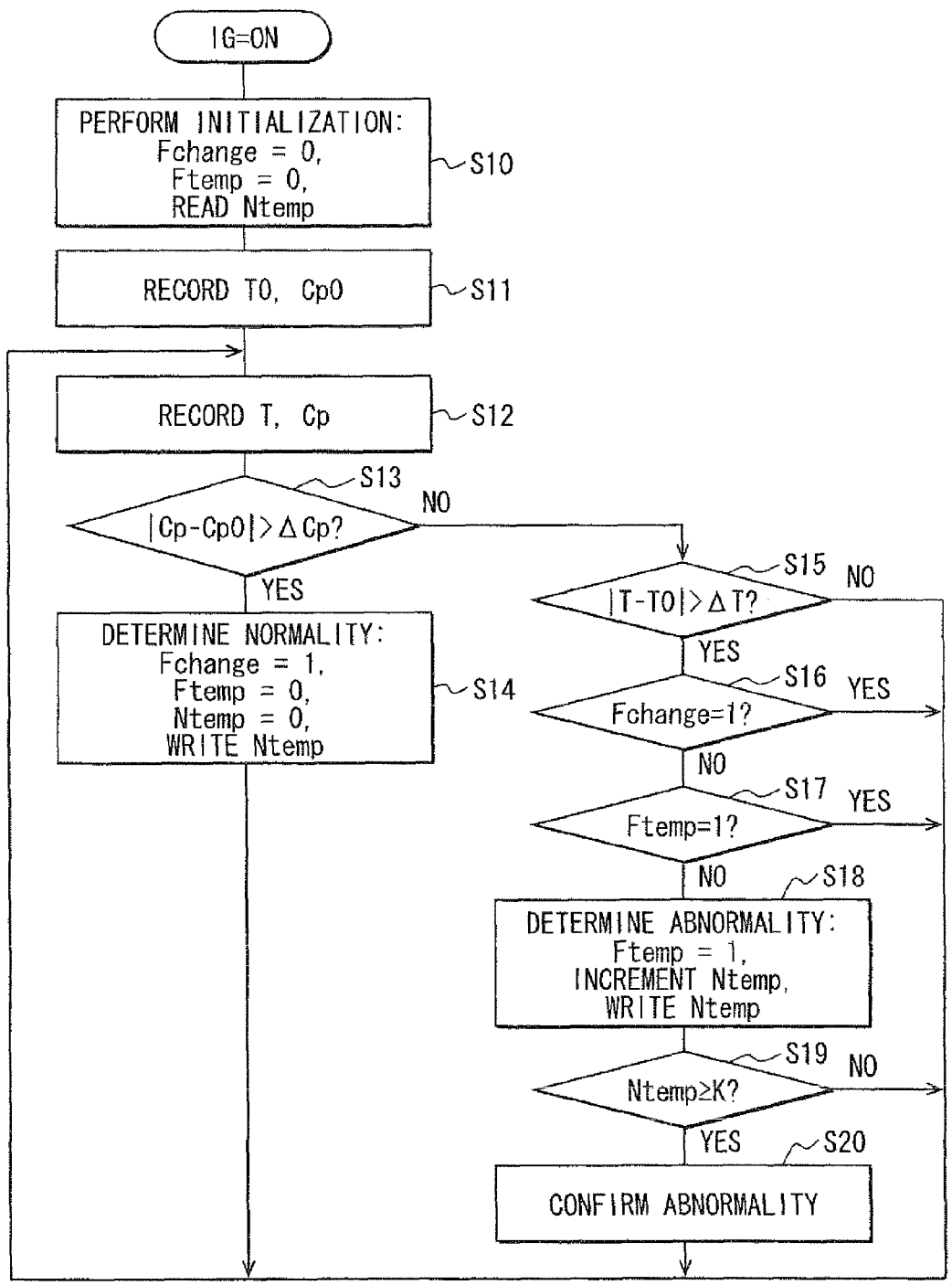
FIG. 6 is a flowchart showing abnormality detection processing of the liquid concentration sensing device according to the first embodiment.

Next, abnormality detection processing performed by the abnormality detecting section according to the present embodiment will be explained based on FIG. 6. The abnormality detection processing is started when an ignition power supply is switched on (IG=ON). First in S10 (S means "Step"), initialization processing is performed. In the initialization processing, both of a change occurrence flag Fchange and a temporary abnormality flag Ftemp, which have been set in the abnormality detection processing performed before the ignition power supply was switched on, are reset to zero (Fchange=0, Ftemp=0). In addition, a temporary abnormality counter Ntemp stored in a memory during the abnormality detection processing performed before the ignition power supply was switched on is read in S10.

In following S11, the fuel temperature sensed by the temperature sensing section 9 is recorded as initial temperature T0. In addition, the capacitance sensed by the capacitance sensing section 8 is recorded as an initial capacitance Cp0 in S11. In following S12, the fuel temperature sensed by the temperature sensing section 9 is recorded as present temperature T. In addition, the capacitance sensed by the capacitance sensing section 8 is recorded as a present capacitance Cp in S12.

In following S13, it is determined whether an absolute value of a difference between the present capacitance Cp and the initial capacitance Cp0 is larger than a first threshold value ΔCp. The first threshold value ΔCp is set based on a map shown in FIG. 7. For example, the first threshold value ΔCp of the fuel, whose ethanol concentration is 100% (i.e., E100), is 5 pF. The first threshold value ΔCp is set based on a fact that the capacitance changes more than 5 pF when the temperature changes by 20 degrees C. in the case where the ethanol concentration is 100% as shown in FIG. 4. In this way, the first threshold value ΔCp is set at a value that is smaller than and close to a change amount of the capacitance, which changes according to the temperature characteristic, for the fuel having the specific concentration. Thus, detection accuracy of the abnormality detecting section can be improved. When the absolute value of the difference between the present capacitance Cp and the initial capacitance Cp0 is larger than the first threshold value ΔCp in S13 (S13: YES), it is determined that a change has occurred in the capacitance, and the processing is shifted to S14. When the absolute value of the difference between the present capacitance Cp and the initial capacitance Cp0 is equal to or smaller than the first threshold value ΔCp in S13 (S13: NO), it is determined that there has been no change in the capacitance and the processing is shifted to S15.

In S14, normality determination processing is performed. In the normality determination processing, the change occurrence flag Fchange is set to 1 (Fchange=1) to record the fact that the capacitance sensing section 8 has detected the change in the capacitance. In addition, it is determined that the capacitance sensing section 8 functions normally, and both of the temporary abnormality flag Ftemp and the temporary abnormality counter Ntemp are reset to 0. The temporary abnormality counter Ntemp is written in.

In S15, it is determined whether an absolute value of a difference between the present temperature T and the initial temperature T0 is larger than a second threshold value ΔT. The second threshold value ΔT is set at 20 degrees C. based on the map shown in FIG. 7. For example, as shown in FIG. 4, in the case of the fuel, whose ethanol concentration is 40%, there is a possibility that it is difficult for the abnormality detecting section to detect the change amount of the capacitance caused by the temperature change in a range smaller than the range between 60 degrees C. and 80 degrees C. Therefore, the second threshold value ΔT is set as a temperature range enabling the abnormality detecting section to detect the change amount of the capacitance that changes according to the temperature characteristic. Thus, the abnormality detecting section can perform correct abnormality determination processing. When the absolute value of the difference between the present temperature T and the initial temperature T0 is larger than the second threshold value ΔT in S15 (S15: YES), it is determined that there has been a change in the fuel temperature and the processing is shifted to S16. When the absolute value of the difference between the present temperature T and the initial temperature T0 is equal to or smaller than the second threshold value ΔT in S15 (S15: NO), it is determined that there has been no change in the fuel temperature and the processing is shifted to S12.

As shown in FIG. 4, the change of the capacitance due to the temperature change in the range of 20 degrees C. is a small value when the ethanol concentration is 40% or lower. Therefore, there is a possibility that it is difficult for the abnormality detecting section to detect the change of the capacitance. Therefore, as shown in FIG. 7, the abnormality detection processing is prohibited when the ethanol concentration is 40% or lower (i.e., when fuel is E40 or lower). More specifically, when the ethanol concentration sensed by the concentration sensing section is 40% or lower, the microcomputer 63 functions as a determination processing prohibiting section and prohibits the abnormality detecting section from performing the abnormality detection processing. Alternatively, the abnormality detection can be performed in the case of the fuel, whose ethanol concentration is 40% or lower, by setting the second threshold value ΔT to be larger than 20 degrees C.

In following S16, it is determined whether the record of the change occurrence flag Fchange is 1. If the normality determination processing of S14 has been performed even once after the ignition power supply was switched on, the abnormality detecting section determines that the result of the abnormality detection processing is the normality determination in the present cycle from the ON to OFF of the ignition power supply. Therefore, if the change occurrence flag Fchange is 1 in S16 (S16: YES), the processing is shifted to S12. If the change occurrence flag Fchange is 0 in S16 (S16: NO), the processing is shifted to S17.

In following S17, it is determined whether the record of the temporary abnormality flag Ftemp is 1. In the abnormality detection processing according to the present embodiment, the temporary abnormality counter Ntemp is incremented at most once in the cycle from the ON to OFF of the ignition power supply. Therefore, if the temporary abnormality flag Ftemp is 1 in S17 (S17: YES), the processing is shifted to S12. If the temporary abnormality flag Ftemp is 0 in S17 (S17: NO), the processing is shifted to S18.

In following S18, the abnormality detecting section determines that an abnormality has occurred in the capacitance sensing section 8 and performs abnormality determination to set the temporary abnormality flag Ftemp at 1. In addition, the abnormality detecting section increments the temporary abnormality counter Ntemp and writes in the temporary abnormality counter Ntemp.

In following S19, it is determined whether a value of the temporary abnormality counter Ntemp is "equal to or larger than" K. K is set at an arbitrary positive integer. By setting K properly, the abnormality detection can be performed surely. If the value of the temporary abnormality counter Ntemp is smaller than K in S19 (S19: NO), the processing is shifted to S12. If the value of the temporary abnormality counter Ntemp is equal to or larger than K in S19 (S19: YES), the processing is shifted to S20.

In S20, the abnormality detecting section performs abnormality confirming processing to confirm the occurrence of the abnormality in the capacitance sensing section 8. The confirmed abnormality is transmitted from the output circuit 64 to the ECU 7. The ECU 7 stops using the signal equivalent to the ethanol concentration in the control of the fuel injection quantity, the ignition timing and the like. In addition, the ECU 7 performs processing for indicating information of the confirmed abnormality on an instrument panel, for example.

In the present embodiment, the microcomputer 63 functions as the abnormality detecting section and performs the abnormality determination to determine that an abnormality has occurred in the capacitance sensing section 8 when the capacitance sensed by the capacitance sensing section 8 does not change although the temperature sensed by the temperature sensing section 9 changes. Since the dielectric constant has such the temperature characteristic that the dielectric constant changes with the temperature. Therefore, the abnormality detecting section can detect the occurrence of the abnormality in the capacitance sensing section 8.

In the present embodiment, the abnormality detecting section sets the temporary abnormality flag Ftemp at 1 and increments the temporary abnormality counter Ntemp as the abnormality determination when the capacitance does not change but the fuel temperature changes. The temporary abnormality counter Ntemp is incremented at most once in the period from the ON to Off of the ignition power supply. The abnormality confirming processing is performed when the temporary abnormality counter Ntemp is incremented continuously K times. In the present embodiment, if the abnormality detecting section detects the change in the capacitance, the abnormality detecting section sets the temporary abnormality flag Ftemp and the temporary abnormality counter Ntemp to 0 to cancel the abnormality determination performed in the past. Therefore, when the state where the capacitance does not change but the fuel temperature changes is a temporary state that is caused because the temperature and the capacitance change in synchronization with each other, the abnormality detecting section can correctly detect the abnormality in the capacitance sensing section 8 by performing the abnormality confirming processing when the abnormality determination continues for a predetermined period.

The ethanol concentration sensor 1 according to the present embodiment transmits a signal for notifying the ECU 7 of the abnormality when the abnormality detecting section performs the abnormality confirming processing. Therefore, the ECU 7 does not use the erroneously sensed ethanol concentration in the engine control and therefore can reduce an influence of a failure of the ethanol concentration sensor 1 to the minimum.

In the present embodiment, the abnormality detecting section determines the existence/nonexistence of the change of the capacitance and then determines the existence/nonexistence of the temperature change. The fuel temperature to be sensed by the temperature sensing section 9 conducts to the thermistor 40 through the board thickness of the second electrode 32. Accordingly, the fuel temperature is sensed in retard of the actual change of the fuel temperature. Therefore, the abnormality detection can be performed correctly by determining the temperature change after determining the change of the capacitance.

Second Embodiment

Figure 8:
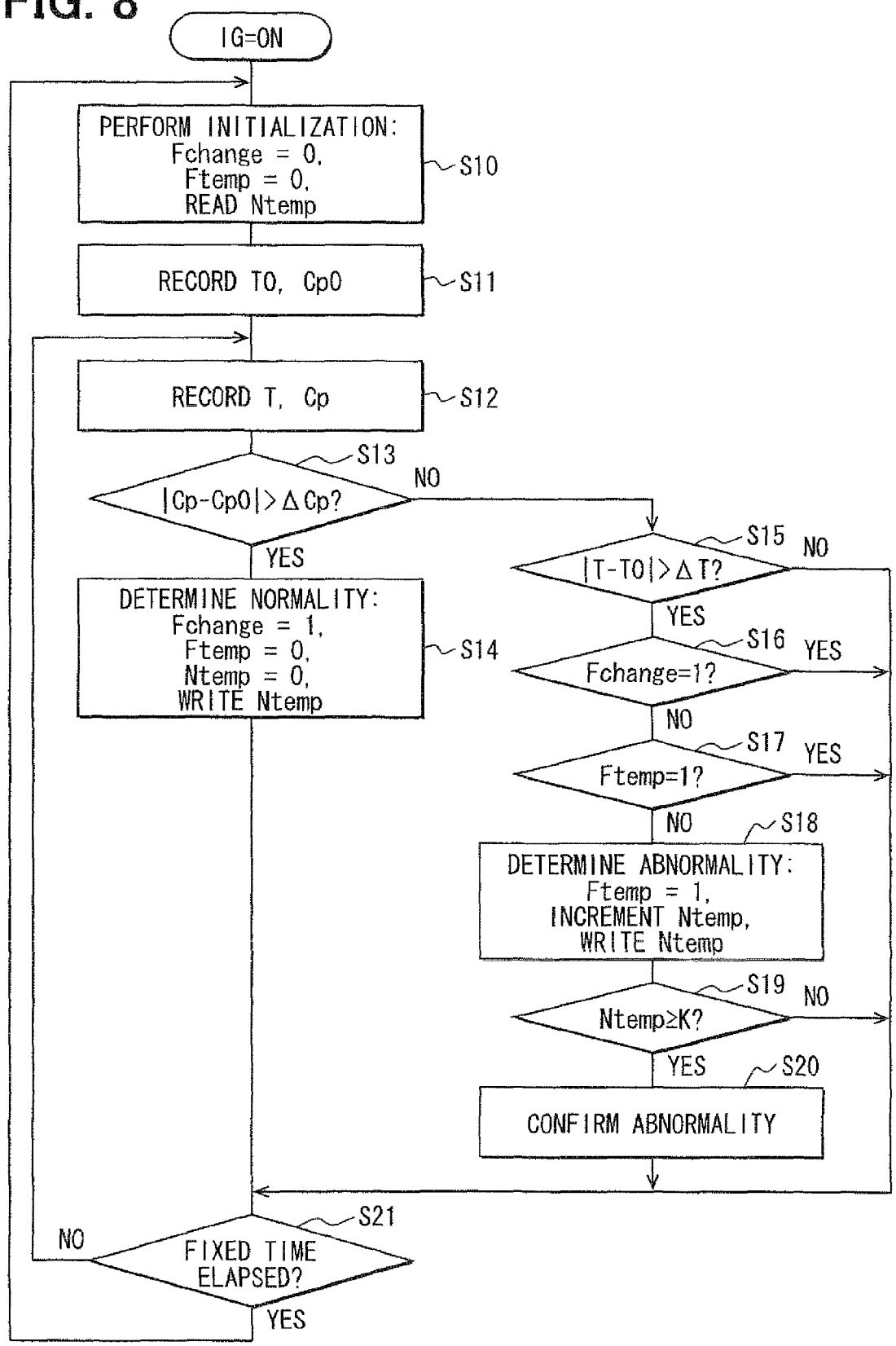
FIG. 8 is a flowchart showing abnormality detection processing of a liquid concentration sensing device according to a second embodiment of the present invention.

Next, abnormality detection processing performed by an abnormality detecting section according to a second embodiment of the present invention will be explained based on FIG. 8. Steps that are substantially identical between the first and second embodiments are denoted with the same reference numeral.

In the present embodiment, it is determined in S21 whether a fixed time has elapsed after the processing of S10. The fixed time can be set arbitrarily. When the fixed time has elapsed in S21 (S21: YES), the processing is shifted to S10. When the fixed time has not elapsed in S21 (S21: NO), the processing is shifted to S12.

In the present embodiment, the abnormality detection processing since the ignition power supply is switched on until the ignition power supply is switched off is performed in segmented cycles of the fixed time. The temporary abnormality counter Ntemp is incremented at most once during the cycle of the fixed time. The abnormality confirming processing is performed when the temporary abnormality counter Ntemp is incremented continuously K times. Therefore, a pace for performing the abnormality confirming processing can be adjusted by setting the fixed time arbitrarily.

Third Embodiment

Figure 9:
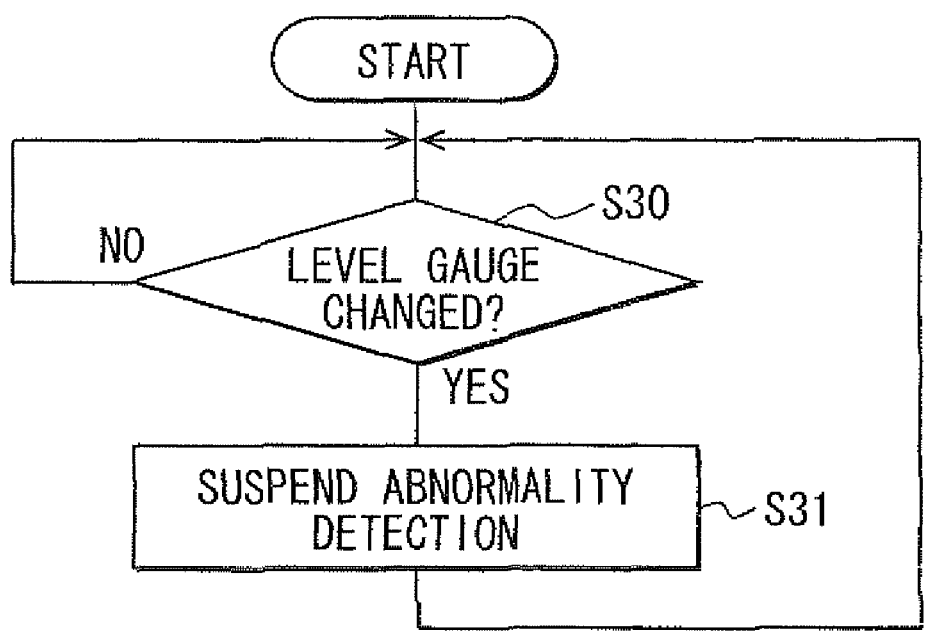
FIG. 9 is a flowchart showing abnormality detection processing of a liquid concentration sensing device according to a third embodiment of the present invention.

Next, abnormality detection suspending processing according to a third embodiment of the present invention will be explained based on FIG. 9.

The CPU executes the programs stored in the RAM, the ROM or the like. Thus, the microcomputer 63 functions as a determination processing suspending section. The determination processing suspending section performs abnormality detection suspending processing for suspending the abnormality detection processing of the abnormality detecting section for a predetermined period when the determination processing suspending section detects that the fuel is replaced. This processing is performed at a predetermined time interval after the ignition power supply is switched on.

First in S30, it is determined whether a fuel level gauge has changed. If the fuel level gauge has changed (S30: YES), the processing is shifted to S31. If there is no change in the fuel level gauge (S30: NO), the processing of S30 is repeated. In following S31, the determination processing suspending section suspends the abnormality detection processing of the abnormality detecting section for the predetermined period.

When there is a change in the fuel level gauge, there is a high possibility that the fuel was fed into the fuel tank 2 in the fuel supply system shown in FIG. 1. In such the case, there is a possibility that the fuel is replaced and the fuel temperature and the capacitance change in synchronization with each other when the fuel is fed into the fuel tank 2. Therefore, when a change occurs in the level gauge, the abnormality determination of the abnormality detecting section is suspended for a predetermined time to prevent the erroneous detection.

The period for suspending the abnormality detection processing of the abnormality detecting section is a period since the change occurs in the fuel level gauge until the fuel injection quantity by the injector 6 becomes equal to or greater than a volume of the fuel pipe 4 between the fuel tank 2 and the ethanol concentration sensor 1. After the period elapses, the determination processing suspending section cancels the suspension of the abnormality detection processing of the abnormality detecting section. Therefore, the ethanol concentration sensing device can prevent the erroneous detection of the abnormality detecting section and can perform correct abnormality detection.

Other Embodiments

The liquid concentration sensing device according to the above-described embodiments is applied to the fuel supply system of the engine for the automobile and senses the concentration of the ethanol contained in the fuel. Alternatively, the liquid concentration sensing device according to the present invention may sense a concentration of a liquid as a sensing object other than the ethanol. The liquid concentration sensing device according to the present invention may be applied to a system other than the fuel supply system of the engine for the automobile.

In the above-described embodiments, the microcomputer 63 of the circuit 60 functions as the abnormality detecting section. Alternatively, the liquid concentration sensing device of the present invention may have an abnormality detecting section in an on-board failure diagnostic system (OBD: On-Board Diagnosis).

In the above-described embodiments, the thermistor 40 is provided inside the second electrode 32. Alternatively, the liquid concentration sensing device of the present invention may have a thermistor 40 that has improved sealing performance and that is immersed in the sensed liquid. In this case, if response of the temperature sensing section to the temperature change of the sensed liquid becomes quicker than response of the capacitance sensing section, the abnormality detecting section may determine the existence/nonexistence of the change in the temperature sensing section before the determination of the existence/nonexistence of the change in the capacitance sensing section.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A liquid concentration sensing device comprising;
   a capacitance sensing means for sensing a capacitance of a sensed liquid;
   a temperature sensing means for sensing temperature of the sensed liquid;
   a concentration sensing means for sensing a concentration of the sensed liquid based on the capacitance sensed by the capacitance sensing means and the temperature sensed by the temperature sensing means; and
   an abnormality detecting means for performing abnormality determination for determining that an abnormality has occurred in the capacitance sensing means when the temperature sensed by the temperature sensing means changes and the capacitance sensed by the capacitance sensing means does not change.

2. The liquid concentration sensing device as in claim 1, wherein
   the abnormality detecting means performs abnormality confirming processing for confirming the occurrence of the abnormality in the capacitance sensing means when the abnormality determination continues for a predetermined period or the abnormality determination occurs multiple times continuously.

3. The liquid concentration sensing device as in claim 1, wherein
   the abnormality detecting means cancels the abnormality determination, which was performed in the past, if the abnormality detecting means detects occurrence of a change in the capacitance sensed by the capacitance sensing means.

4. The liquid concentration sensing device as in claim 1, wherein
   the abnormality detecting means determines existence or nonexistence of a change in certain one of sensing results of the capacitance sensing means and the temperature sensing means, the certain one having quicker response to a change in the sensed liquid, and then, the abnormality detecting means determines existence or nonexistence of a change in the other one of the sensing results, the other one having slower response to the change in the sensed liquid.

5. The liquid concentration sensing device as in claim 1, wherein
   the abnormality detecting means determines that the capacitance sensed by the capacitance sensing means has not changed if the change amount of the capacitance sensed by the capacitance sensing means is equal to or smaller than a first threshold value set at a value smaller than a change amount of the capacitance, which occurs with respect to a predetermined temperature range in the case of the sensed liquid having a specific concentration.

6. The liquid concentration sensing device as in claim 1, wherein
   the abnormality detecting means determines that the temperature sensed by the temperature sensing means has changed when a change amount of the temperature sensed by the temperature sensing means is larger than a second threshold value, which is set as a temperature range enabling the abnormality detecting means to detect the change amount of the capacitance that changes according to a temperature characteristic in the case of the sensed liquid having a specific concentration.

7. The liquid concentration sensing device as in claim 1, further comprising:
   a determination processing prohibiting means for prohibiting the abnormality detecting means from performing the abnormality determination when the concentration of the sensed liquid sensed by the concentration sensing means is equal to or lower than a predetermined concentration, below which the abnormality detecting means cannot detect the change in the capacitance due to the temperature characteristic.

8. The liquid concentration sensing device as in claim 1, further comprising:
   a determination processing suspending means for suspending the abnormality determination of the abnormality detecting means for a predetermined period when the determination processing suspending means detects that the sensed liquid is replaced.

* * * * *